United States Patent [19]

Farrar et al.

[11] Patent Number: 4,996,251
[45] Date of Patent: Feb. 26, 1991

[54] POLYMERIC COMPOSITIONS AND THEIR PRODUCTION

[75] Inventors: David Farrar; Peter Flesher, both of West Yorkshire; Peter R. B. Lawrence, London, all of Great Britain

[73] Assignee: Allied Colloids Ltd., Great Britain

[21] Appl. No.: 308,836

[22] Filed: Feb. 9, 1989

[30] Foreign Application Priority Data

Feb. 10, 1988 [GB] United Kingdom ............... 8803064
Feb. 10, 1988 [GB] United Kingdom ............... 8803066

[51] Int. Cl.$^5$ .................. C02C 1/02; C02C 5/10; C08F 6/00; C08F 20/56
[52] U.S. Cl. ......................... 524/17; 524/21; 524/827; 526/199; 528/492; 435/228; 435/262
[58] Field of Search .................. 524/17, 21, 827; 526/199; 528/492; 435/228, 262

[56] References Cited

U.S. PATENT DOCUMENTS 4,786,679 11/1988 Wetegrove et al. ............... 526/199

FOREIGN PATENT DOCUMENTS 62779A 7/1978 Japan .
62780A 7/1978 Japan .

*Primary Examiner*—Nathan M. Nutter
*Attorney, Agent, or Firm*—Ostrolenk, Faber, Gerb & Soffen

[57] ABSTRACT

The invention provides a substantially dry particulate composition comprising a polyacrylamide and an amidase. An aqueous composition made by dispersing this into water will then have a satisfactorily low content of residual acrylamide even if the initial polymer was contaminated with monomer. The composition is made by blending dry polyacrylamide particles with the amidase.

17 Claims, No Drawings

POLYMERIC COMPOSITIONS AND THEIR PRODUCTION

This invention relates to the provision of polyacrylamides with reduced monomer impurity levels.

Polyacrylamides may contain small amounts of residual monomeric acrylamide and this is undesirable. It is known that acrylamide can be converted to acrylic acid by the action of an amidase. As an example, in JP-A-52045854 and JP-A-54041984 acrylamide is polymerised in the soil so as to stabilise the soil and contamination of the stabilised soil by free monomer is reduced by injecting amidase into the soil with the acrylamide that is to be polymerised. However this process is not very satisfactory since monomer can escape to the environment and monomer may be converted to acrylic acid before polymerisation, thus tending to form polyacrylic acid, and it is necessary for the operative to supply the enzyme as well as the polymerising solution.

Various other processes are known in which the user of the polymer reduces the residual acrylamide content in a preformed solution of polyacrylamide. Such processes are described in, for instance, JP-A-53086078, JP-A-53086079 and JP-5209447. For instance the latter includes an example in which 10 g anionic polyacrylamide having a monomer concentration of 500 ppm is diluted in water to 10 litres in the presence of enzyme solution, and the acrylamide monomer content is thus reduced. All these processes suffer from the disadvantage that the polymer solution must be made up first and the user, who has made up the solution, must then add the enzyme to it.

Polyacrylamide is generally supplied by the manufacturer to the user in the form of a powder or as a dispersion in water-immiscible liquid and it would be desirable for the manufacturer to be able to supply a material that, when diluted with water by the user, had a suitably low residual monomer content.

In U.S. Pat. No. 4,687,807 amidase is added to a water-in-oil emulsion of polyacrylamide which is then subjected to pH adjustment and/or heating and/or inert gas sparging and/or adding a chemical reducing agent. The overall process conditions, including this final step, are said to cause the amount of free acrylamide monomer in the aqueous emulsion to be reduced significantly.

It is stated in the patent that the amount of polymer in the emulsion may be from 5 to 60% and the amount of water from 20 to 90%. Thus the amount of water is always at least 33% by weight based on dry polymer. In practice it is well known that water-in-oil emulsions do, in practice, always contain an amount of water within a much narrower range, and in particular the amount of water is generally within the range of 30 to 55% (which is stated in U.S. Pat. No. 4,687,807 as being the preferred amount of water). The presence of these significant amounts of water during the process are clearly essential to the process of U.S. Pat. No. 4,687,807 as the amidase would only effectively consume acrylamide monomer in an aqueous medium. The patent warns that if the emulsion is being heated then temperatures above 60° C. can be used only as long as deactivation does not become significant, and so this again indicates the criticality of maintaining the water in the emulsion.

We are particularly concerned with the production of substantially dry, particulate polyacrylamide compositions and with the desirability of ensuring that solutions made from such compositions have a very low acrylamide monomer content even if the initial polymer is contaminated with, for instance, 500 ppm or more, e.g., 1000 ppm to 5000 ppm, acrylamide monomer (based on dry polymer). Accordingly none of the prior art on the incorporation of amidase into aqueous polyacrylamide compositions is of any relevance.

According to the invention, we provide a substantially dry composition comprising a polyacrylamide and an amidase.

The amount of water in the substantially dry composition is generally below 20%, usually below 15% and preferably below 10% by weight of the polymer in the composition.

The amidase can have been blended with the polymer while the polymer is in the form of an aqueous product, in which event it may have reduced the acrylamide monomer content whilst the product is aqueous, and prior to drying to a substantially dry particulate composition. Such processes are described in application 308,832 filed even data herewith. At this stage the composition may have, for instance, below 1000 parts monomer per million parts polyacrylamide.

Preferably however the polyacrylamide is produced in the form of substantially dry particles and the amidase is mixed with these to produce a substantially dry particulate composition, the amidase in the composition being effective, when the composition is dispersed into water for two hours at 25° C., to reduce the content of acrylamide monomer.

In this preferred system, there may be some reduction in acrylamide monomer content within the substantially dry particulate composition but it is generally satisfactory in the invention for the acrylamide monomer content to remain substantially unchanged in the composition after addition of the amidase. However when the composition is subsequently dispersed into water, so as to allow solution or swelling of the polymer particles in the water, the amidase will interact with acrylamide monomer, for instance to produce acrylic acid, so that the final solution has the desired very low value of acrylamide monomer, generally below 100 ppm monomer, based on polymer. Preferably the solution is conducted at temperatures of 20° to 55° C., often slightly elevated temperatures, so as to promote the consumption of monomer by the amidase.

The amidase that is to be added to the substantially dry polymer particles may be in aqueous form, for instance as a solution, emulsion or dispersion. The amount of water introduced in this manner is preferably such that the mixed composition that is obtained is substantially dry, as explained above although it is possible for the initial mixture to have a slightly higher content, provided the particles still remain relatively dry, and for the composition then to be dried sufficiently to make it substantially dry and storage stable. Preferably however, the amount of drying that is applied to the composition is kept to a minimum and any drying that is applied is at relatively low temperatures, so as to avoid the risk of damaging the amidase by excessive heat.

When the amidase is applied as an aqueous composition, some or all of the polyacrylamide particles will generally then have amidase coated or absorbed on to their surfaces.

A preferred way of making the compositions of the invention is by blending the polyacrylamide particles with particles comprising amidase.

These particles are preferably freeze dried amidase particles for instance as described in JP-54041984 filed 9th April 1979 (Japanese patent No. 135,191 of 1980) or the particles may be of amidase immobilised in polymer gel (for instance calcium alginate or polyacrylamide gel) or in some other water soluble encapsulating matrix or coating.

The amount of the amidase particles or the amidase aqueous solution will be selected according to the concentration of amidase in the particles or solution, the activity of the amidase and the amount of monomer. Suitable amounts that are effective for achieving the desired reduction can easily be found by routine optimisation. Typically it is 0.05 to 5%, often 0.1 to 1% dry weight enzyme based on dry weight polymer.

The composition of the invention may be a powdered composition having a particle size at least 50% by weight above 30 $\mu$m. Generally at least 90% by weight of the particles are above 30 $\mu$m, preferably above 50 $\mu$m. Generally at least 90% by weight are below 2 mm, preferably below 1 mm, most preferably below 500 $\mu$m. It is often preferred that at least 90% by weight are in the range 50 to 200 $\mu$m. Thus polyacrylamide can be put into the form of particles having the desired size in conventional manner and then can be blended with aqueous amidase or dry mixed with particulate amidase.

A preferred composition of the invention is a composition in which the particles have a size at least 50% below 30 $\mu$m and are present as a substantially anhydrous dispersion in non-aqueous liquid. The amount of water in this dispersion is generally below 15%, and usually below 10%, by weight of the dispersion.

The dispersion of the invention is made by forming a substantially anhydrous dispersion in non-aqueous liquid of particles of polyacrylamide at least 50% by weight being below 30 $\mu$m and which contains water in an amount below the maximum specified above, and then distributing the amidase throughout the dispersion.

Preferably the amidase is distributed substantially uniformly throughout the dispersion. It may be present as particles separate from the polyacrylamide particles of the dispersion. For instance solid, generally substantially dry, freeze dried or other particles containing the amidase may be blended into the dispersion.

A preferred way of incorporating the amidase throughout the dispersion is to form the substantially anhydrous dispersion of polyacrylamide and then to blend aqueous amidase into the dispersion. The amidase may be added as an aqueous solution, optionally with a water-in-oil emulsifying agent, that is then stirred into the dispersion, or the amidase may be added as an aqueous emulsion in a non-aqueous liquid that is miscible with the non-aqueous liquid of the dispersion. The substantially dry polymer particles will tend to attract the aqueous amidase particles that are emulsified into the non-aqueous liquid with the result that the aqueous amidase will tend to be adsorbed on to the surfaces of the polymer particles.

This addition of aqueous amidase will result in an increase in the water content of the dispersion and so normally the dispersion is dried to a water content of below 10%, and often below 5%, by weight based on the dispersion, and often to a water content of below 10%, generally below 5% and often below 3% based on the polymer. Upon addition of the aqueous amidase solution, or the aqueous emulsion of amidase, the water content is then increased slightly, but can still be within the low values that are used in the invention.

The polymer dispersion may be made by dispersing pre-formed substantially dry polymer particles into the non-aqueous liquid. These particles may be formed by comminution, in the non-aqueous liquid, of larger substantially dry polymer particles (for instance mainly or wholly above 50 $\mu$m, often 100 $\mu$m to 1 mm). Usually, however, the polymer particles that are introduced have the desired final size of at least 50% below 30 $\mu$m. They can be, for instance, reverse phase microbeads but preferably they are fines separated from polymer gel, for instance obtained during the comminution of bulk or bead gel or separated from beads obtained by reverse phase polymerisation. When the polymer is formed before addition to the non-aqueous liquid, it generally has a water content below 10% at the time of addition to the liquid and, in the final dispersion, generally has at least 90% of the particles in the range 1 to 40 $\mu$m, often at least 50% in the range 10 to 30 $\mu$m.

Instead of using preformed polymer, it is particularly preferred in the invention to perform the polymerisation, and form the polymer particles, in the non-aqueous liquid, for instance by conducting reverse phase polymerisation of aqueous monomer or monomer blend in the liquid, generally as a reverse phase suspension polymerisation. The particle size of the polymer particles is then generally below 10 $\mu$m, usually at least 90% below 3 $\mu$m and often mainly below 1 $\mu$m.

When the polymer particles are formed in the dispersion in the presence of water, it is necessary to dry the dispersion before adding the amidase. Methods of drying water-in-oil polymer emulsions are known and can be used in the invention. Preferably the drying is by azeotroping.

Instead of blending amidase particles into a substantially anhydrous dispersion of polymer particles, it is also possible to blend the substantially dry polymer particles into a dispersion or emulsion of the amidase particles.

In order to stabilise the polymer dispersions and/or the polymerisation dispersions and/or the amidase emulsions or dispersions, conventional emulsifiers and/or stabilisers may be used. Thus the initial formation of a dispersion in non-aqueous liquid of aqueous monomer may be facilitated by the use of a water-in-oil emulsifying agent and the stability of a polymer dispersion may be promoted by the incorporation of an amphipathic stabiliser.

The non-aqueous liquid can be any convenient hydrocarbon, chlorinated hydrocarbon or other non-aqueous liquid suitable for the formation of polymer dispersions. Suitable non-aqueous liquids, emulsifiers and stabilisers are described in, for instance, EP 126528. When using preformed polymer particles it may be desirable to stabilise them by the incorporation in the non-aqueous liquid phase of a thickener that is insoluble or non-swellable in water, for instance a Bentone clay or, preferably, a polymeric thickener, for instance as described in EP 0161926. Suitable amounts of amphipathic stabilisers, if present, are in the range 0.2 to 10% based on polymer. Suitable amounts of water-in-oil emulsifier, if present, are 0.2 to 3%, based on monomer. Suitable amounts of other stabilisers, if present, are 1 to 15%, based on polymer.

The amount of polymer, based on non-aqueous liquid, is often in the range 0.5 to 2 parts per part non-aqueous liquid.

The amount of amidase and the materials that are used is preferably such that the content of acrylamide monomer, measured as described above, is often below 1000 ppm and frequently below 500 ppm and preferably 100 ppm based on dry polymer. Values of below 50 ppm and even below 5 ppm can be obtained in the invention. Best results require that the value is below 1 ppm.

The polyacrylamide that is treated in the invention can be a homopolymer of acrylamide or it can be a copolymer with one or more ethylenically unsaturated non-ionic, anionic or cationic monomers. The amount of comonomer can be from 1 to 99% by weight but is usually below 90% and often below 70% by weight. Typical non-ionic monomers include styrene and N-vinyl pyrollidone. Typical anionic monomers are ethylenically unsaturated carboxylic and sulphonic monomers, especially (meth) acrylic acid and 2-acrylamido-2-methyl propane sulphonic acid. Typical cationic monomers are diallyl dimethyl ammonium chloride and dialkylaminoalkyl (meth) -acrylates and -acrylamides, generally as acid addition or quaternary ammonium salts.

The polymer can be water soluble or water insoluble but swellable, for instance as a result of cross linking, e.g., by copolymerisation with poly-ethylenically unsaturated cross linking agent in known manner.

The polymer may be polymerised to any convenient molecular weight at which it can form powdered particles. Accordingly the molecular weight will usually be above about 100,000 and often above 500,000. Values in the range 1 to 30 million or higher often being preferred. The polymer may have been made by any convenient polymerisation, for instance bulk gel polymerisation followed by comminution and drying or by reverse phase bead polymerisation followed by drying (when the particles are relatively coarse) or by reverse phase suspension polymerisation, when the particles are very small.

The content of monomer in the initial polymer can be quite low, e.g., 300 ppm, but often it is above 500 ppm and frequently above 1000 ppm (based on the dry weight of polymer). It is usually below 5000 ppm but can be higher. The process of the invention typically reduces monomer content by at least one third, preferably at least two thirds and most preferably by at least three quarters of initial monomer content.

Prior to the invention it has been necessary to select initiator and polymerisation conditions so as to minimise residual monomer and an inevitable consequence has been that molecular weight is depressed. As a result of the invention the polymerisation can be conducted to give maximum molecular weight and the resultant high level of residual monomer can then be reduced by the process of the invention.

Any of the amidase that are known for converting acrylamide to acrylic acid can be used, including any of those mentioned in the literature quoted above. Particularly preferred are *Brevibacterium ammoniagenes* especially those described in JP-A-53086078. Preferably the seed strain of *B. ammoniagenes* is cultured at 25°-35° C. and pH 6.5-8.5 in a liquid culture medium containing carbon source, nitrogen source, inorganic salts and other nutrients. After cultivation the bacterial body is separated by filtration and the crude enzyme can be obtained by drying the bacterial body by acetone or by freeze drying and breaking the bacterial cells by mashing in buffer solution or subjecting to supersonic waves. Preferred species are ATCC 1641, ATCC 6871 and ATCC 6872. Other suitable amidases are those described in JP-A-53086079. These include the intracellular enzyme of *Brevibacterium acetylicum, B. helvorum, B.*
*lucinophagum, B. linens* or *B. vitarumen*. They may be cultured in the similar manner. Preferred materials are *B. acetylicum* ATCC 953, *B. helvolum* ATCC 11822, *B. lucinophagum* ATCC 13809, *B. linens* ATCC 8377 and *B. vitarumen* ATCC 10234.

Other suitable enzymes are mixtures of Bacillus and Pseudomonas, e.g., *Bacillus sphaericus* IAM 1286 and *Pseudomonas putrefaciens* ATCC 8071 or mixtures of Brevibacterium (except for *B. ammoniagenes*) and Pseudomonas, e.g., *B. acetylicum* ATCC 953 and *P. putrefaciens* ATCC 8071 or mixtures of Brevibacterium and Bacillus, e.g., *Bacillus brevis* IAM 1031 and *Brevibacterium ammoniagenes* IAM 1641, as described in, respectively, JP-A-52099281, JP-A-5294473 and JP-A-52094470.

It will be appreciated that the amidase may be pure or semi-pure or may be bacterial cells or any other fraction having the desired enzyme activity for converting acrylamide. Cofactors and other materials that promote enzymatic activity may be included in the compositions of the invention. Generally they are introduced in the aqueous or particulate enzyme composition.

The following are some examples.

EXAMPLE 1

An anionic polyacrylamide having high molecular weight is made by bulk gel polymerisation in conventional manner and the resultant gel is dried and comminuted in conventional manner. Fines having a particles size mainly below 30 μm and a water content of below 10% are sieved from the comminuted gel and are dispersed in a hydrocarbon oil thickened with a dispersion stabiliser as described at page 18 line 25 to 35 of EP 0161926A. Freeze dried amidase is stirred into the dispersion (about 0.5% dry on dry).

When the product is stirred into water sufficient to obtain a solution, the resultant solution is found to have an acrylamide content of below 40 ppm, even though the starting polymer would have given an acrylamide content substantially above 100 ppm.

EXAMPLE 2

A cationic polymeric flocculant is made by reverse phase polymerisation of aqueous acrylamide with aqueous methyl chloride quaternised dimethylaminoethyl acrylate, in conventional manner and in the presence of an amphipathic stabiliser as described in EP 126528. The resultant water-in-oil emulsion, having a water content of around 50% based on polymer or 30% based on total dispersion, is subjected to azeotropic distillation to a water content of below 5%, based on polymer, all in conventional manner.

An emulsion in oil of aqueous amidase is then stirred into the dispersion, the amidase emulsion having proportions such that the water content of the dispersion (based on polymer) is about 6%.

Oil-in-water emulsifier is added and the resultant substantially anhydrous dispersion is stirred into water. Even though the free monomer content, based on polymer, in the initial dispersion is above 100 ppm, the free monomer content in the resultant solution is below 20 ppm.

EXAMPLE 3

A cationic polymer flocculant is prepared by bulk gel polymerisation. Thus, 142.8 g of 50% acrylamide solution in water and 43.7 g of 70% solution in water of methyl chloride quaternised dimethylamino-ethylacrylate are mixed with 113.5 g of water and the solution adjusted to pH 4 with hydrochloric acid. After cooling to 5° C. the solution is degassed with nitrogen and the polymerisation initiated using redox initiator (KBrO$_3$/Na$_2$SO$_3$) and thermal initiator (ammonium persulphate. Once the full heat rise has been obtained the gel polymer is processed to yield gel chips of 1-4 mm in size. The chips are placed in a hot air stream at 70° C. to yield a dry product of 7% moisture. The dried chips are ground using a domestic coffee grinder to yield product of 850-150 μm in size.

A 1% solution of the polymer powder in water yields a clear, viscous lump free solution. The intrinsic viscosity of the polymer measured in 1 M NaCl at 25° C. is 9, at pH 7. The free acrylamide content is determined by GLC is 0.12%.

50 g of the dry polymer chip is placed in a four ounce glass bottle and sufficient amidase (0.2-0.5% dry on dry) added. The container is capped and tumbled to intimately mix the components.

When the product is stirred into water sufficient to obtain a solution, an acrylamide-free solution is prepared.

EXAMPLE 4

An aqueous solution of acrylamide 63 g and acrylic acid 21 g in water is pH adjusted to pH 6 with sodium hydroxide liquor 46% and the total solution weight adjusted to 300 g with water. After cooling to 5° C. and degassing the solution with nitrogen the polymerisation is initiated using the ferrous ammonium sulphate/ammonium persulphate redox pair with AZDN as thermal initiator. The product gel is processed, (cut, dried and ground) as for example 1. The anionic flocculant polymer product contained 5% moisture and 0.152% free acrylamide yielded a lump free solution and is of intrinsic viscosity 16 in 1 M NaCl at pH 7.

60 g of the dry polymer is placed in a domestic blender and the chip suspended in air by operation of the blender. The required amount of amidase as a concentrated aqueous or H$_2$O/MeOH solution (3 mls) is introduced into the blender. The agitation produced an even coating of the additive. The polymer chip is redried to produce the final product.

Upon stirring into water, an acrylamide-free solution is obtained.

What is claimed is:

1. A dispersion in non-aqueous liquid of particles of acrylamide polymer at least 50% by weight below 30 μm, wherein the water content of the dispersion is below 15 by weight based on the total weight of the dispersion and the dispersion also contains an amidase that is effective, when the dispersion is dispersed into water for 2 hours at 25° C., to reduce the content of acrylamide monomer.

2. A composition according to claim 1 formed by providing the dispersion of particles of acrylamide polymer in the non-aqueous liquid wherein the water content of the dispersion is below 15% by weight, and then blending amidase into the dispersion.

3. A dispersion according to claim 2 made by mixing with polyacrylamide particles and emulsion of amidase in oil.

4. A dispersion according to claim 3 containing a amphipathic stabilizer.

5. A dispersion according to claim 4 having a water content below 10% by weight.

6. A dispersion according to claim 4 made by mixing amidase with polyacrylamide having less than 5% by weight water.

7. A composition according to claim 1 which provides an amount of acrylamide monomer of below 1000 parts monomer per million parts polyacrylamide when determined by dispersing the composition in water at 25° C. for two hours.

8. A composition according to claim 7 in which the amount is below 100 parts per million monomer.

9. A dispersion in non-aqueous liquid of particles of acrylamide polymer at least 90% by weight below 3 μm wherein the water content of the dispersion is below 15% by weight based on the total weight of the dispersion and the dispersion also contains an amidase that is effective, when the dispersion is dispersed into water for 2 hours at 25° C., to reduce the amount of acrylamide monomer, and in which the dispersion has been made by reverse phase polymerization of the acrylamide polymer particles in the non-aqueous liquid followed by azeotropic drying of the resultant dispersion followed by addition of the amidase.

10. A dispersion according to claim 9 made by mixing with polyacrylamide particles and emulsion of amidase in oil.

11. A dispersion according to claim 10 containing a amphipathic stabilizer.

12. A dispersion according to claim 11 having a water content below 10% by weight.

13. A dispersion according to claim 11 made by mixing amidase with polyacrylamide having less than 5% by weight water.

14. A dispersion according to claim 1 made by mixing with polyacrylamide particles and emulsion of amidase in oil.

15. A dispersion according to claim 1 containing a amphipathic stabilizer.

16. A dispersion according to claim 1 having a water content below 10% by weight.

17. A dispersion according to claim 1 made by mixing amidase with polyacrylamide having less than 5% by weight water.

* * * * *